United States Patent
Narimatsu

(10) Patent No.: US 6,923,770 B2
(45) Date of Patent: Aug. 2, 2005

(54) PULSE-WAVE-CHARACTERISTIC-POINT DETERMINING APPARATUS, AND PULSE-WAVE-PROPAGATION-VELOCITY-RELATED-INFORMATION OBTAINING APPARATUS EMPLOYING THE PULSE-WAVE-CHARACTERISTIC-POINT DETERMINING APPARATUS

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 652 days.

(21) Appl. No.: 10/121,657

(22) Filed: Apr. 15, 2002

(65) Prior Publication Data

US 2003/0069490 A1 Apr. 10, 2003

(30) Foreign Application Priority Data

Oct. 10, 2001 (JP) ...................................... 2001-312209

(51) Int. Cl.[7] .............................................. A61B 5/02
(52) U.S. Cl. ...................................................... 600/500
(58) Field of Search ................................. 600/500–503, 600/490, 492–496

(56) References Cited

U.S. PATENT DOCUMENTS 3,915,156 A * 10/1975 Wastl et al. ................. 600/501

6,368,282 B1 * 4/2002 Oka et al. .................... 600/485
6,447,458 B1 * 9/2002 Farrell et al. ................ 600/500

FOREIGN PATENT DOCUMENTS

EP          1 095 611 A1      5/2001

OTHER PUBLICATIONS

Fetics et al., "Parametric Model Derivation of Transfer Function for Noninvasive Estimation of Aortic Pressure by Radial Tonometry", IEEE Transactions on Biomedical Engineering, vol. 46, No. 6, Jun., 1999.

* cited by examiner

Primary Examiner—Robert L. Nasser
Assistant Examiner—Navin Natnithithadha
(74) Attorney, Agent, or Firm—Oliff & Berridge, PLC

(57) ABSTRACT

An apparatus for determining a characteristic point of a pulse wave detected from a living subject, the apparatus including a pulse-wave detecting device which detects a first pulse wave from a prescribed portion of the subject, a pulse-wave modifying device for modifying a waveform of the first pulse wave detected by the pulse-wave detecting device, according to a predetermined relationship between first pulse wave, and second pulse wave whose characteristic point is clear, and a characteristic-point determining device for determining a characteristic point of the modified waveform of the first pulse wave.

9 Claims, 6 Drawing Sheets

US 6,923,770 B2

PULSE-WAVE-CHARACTERISTIC-POINT DETERMINING APPARATUS, AND PULSE-WAVE-PROPAGATION-VELOCITY-RELATED-INFORMATION OBTAINING APPARATUS EMPLOYING THE PULSE-WAVE-CHARACTERISTIC-POINT DETERMINING APPARATUS

BACKGROUND OF THE INVENTION

1. Field of the Invention

The present invention relates to a pulse-wave characteristic-point determining apparatus which determines a characteristic point of a pulse wave and which is needed, e.g., to calculate a pulse-wave propagation velocity, and also relates to a pulse-wave-propagation-velocity-related-information obtaining apparatus which obtains pulse-wave-propagation-velocity-related information and which employs the pulse-wave-characteristic-point determining apparatus. The pulse-wave-propagation-velocity-related information is information that is related to a velocity at which a pulse wave propagates through an artery between two prescribed portions of a living subject; such as a pulse-wave propagation velocity itself, or a pulse-wave propagation time.

2. Related Art Statement

Obtaining pulse-wave-propagation-velocity-related information involves detecting, from a living subject, two heartbeat-synchronous signals, e.g., a pulse wave, such as a brachial-artery pulse wave, and a heart sound, and determining a time difference between respective times of occurrence of respective characteristic points of respective waveforms of the two heartbeat-synchronous signals. This time difference is the above-mentioned pulse-wave propagation time, and the above-mentioned pulse-wave propagation velocity is obtained by dividing the pulse-wave propagation time by the distance of propagation. Thus, obtaining pulse-wave-propagation-velocity-related information needs determining respective characteristic points of respective waveforms of two heartbeat-synchronous signals. Each characteristic point may be a notch, a rising point, or a maximal point of a heartbeat-synchronous pulse of a pulse wave. The notch is a point where the amplitude of the pulse starts increasing after having decreased following the maximal point.

A time difference between the rising point and the notch corresponds to a time duration in which the left ventricle of the heart contracts, i.e., an ejection period in which blood is ejected from the heart. Thus, the ejection period can be obtained by determining the rising point and the notch as the characteristic points of the pulse wave.

Thus, the pulse-wave-propagation-velocity-related information or the like is obtained based on the times of occurrence of characteristic points of waveforms. Therefore, obtaining accurate pulse-wave-propagation-velocity-related information needs determining accurate times of occurrence of characteristic points.

However, there have been some cases where accuracy of determination of those characteristic points is not sufficiently high. In particular, the degree of clarity of the notch decreases as the distance from the center of the subject increases. For example, for some patients, a pulse wave detected from their upper arm, i.e., a brachial-artery pulse wave shows a considerably clear notch; but it does not for other patients. If the notch is unclear, it is natural that pulse-wave-propagation-velocity-related information or the like obtained based on the notch should be inaccurate. Hence, conventionally, it has been practiced, for accurately determining a time of occurrence of a notch, to pass a signal containing a pulse wave, through a band-pass filter which allows passing of only a signal component having frequencies of the notch, so as to emphasize the notch and determine the location of the notch on the waveform of the pulse wave. However, this method is effective in only those cases where a notch is identifiable to some degree before it is passed through the band-pass filter, and not effective in other cases.

SUMMARY OF THE INVENTION

It is therefore an object of the present invention to provide a pulse-wave-characteristic-point determining apparatus which can accurately determine a characteristic point of a pulse wave, and a pulse-wave-propagation-velocity-related-information obtaining apparatus which employs the pulse-wave-characteristic-point determining apparatus.

The above object has been achieved by the present invention. According to a first aspect of the present invention, there is provided an apparatus for determining a characteristic point of a pulse wave detected from a living subject, the apparatus comprising a pulse-wave detecting device which detects a first pulse wave from a prescribed portion of the subject; a pulse-wave modifying means for modifying a waveform of the first pulse wave detected by the pulse-wave detecting device, according to a predetermined relationship between first pulse wave, and second pulse wave whose characteristic point is clear; and a characteristic-point determining means for determining a characteristic point of the modified waveform of the first pulse wave.

According to this invention, the pulse-wave modifying means modifies the waveform of the first pulse wave actually detected by the pulse-wave detecting device, according to the predetermined relationship between first pulse wave and second pulse wave whose characteristic point is clear. Therefore, even if the characteristic point of the waveform of the actually detected first pulse wave may not be clear, the characteristic point of the modified waveform of the first pulse wave is clear. Thus, the characteristic-point determining means can accurately determine the characteristic point of the modified waveform of the first pulse wave.

According to a second aspect of the present invention, there is provided an apparatus for obtaining pulse-wave-propagation-velocity-related information that is related to a velocity at which a pulse wave propagates in a living subject, the apparatus comprising a pulse-wave detecting device which detects, as a first heartbeat-synchronous signal, a first pulse wave from a first prescribed portion of the subject; a pulse-wave modifying means for modifying a waveform of the first pulse wave detected by the pulse-wave detecting device, according to a predetermined relationship between first pulse wave, and second pulse wave whose characteristic point is clear; a characteristic-point determining means for determining a characteristic point of the modified waveform of the first pulse wave; a heartbeat-synchronous-signal detecting device which detects, from a second prescribed portion of the subject that is different from the first prescribed portion, a second heartbeat-synchronous signal; and a pulse-wave-propagation-velocity-related-information means for obtaining the pulse-wave-propagation-velocity-related information, based on a time of occurrence of the determined characteristic point of the modified waveform of the first pulse wave and a time of occurrence of a prescribed point of the second heartbeat-synchronous signal detected by the heartbeat-synchronous-signal detecting device.

According to this invention, the characteristic-point determining means can accurately determine the characteristic point of the modified waveform of the first pulse wave, and accordingly the pulse-wave-propagation-velocity-related-information means can accurately obtain the pulse-wave-propagation-velocity-related information, based on the time of occurrence of the accurately determined characteristic point of the modified waveform of the first pulse wave and the time of occurrence of the prescribed point of the second heartbeat-synchronous signal detected by the heartbeat-synchronous-signal detecting device.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
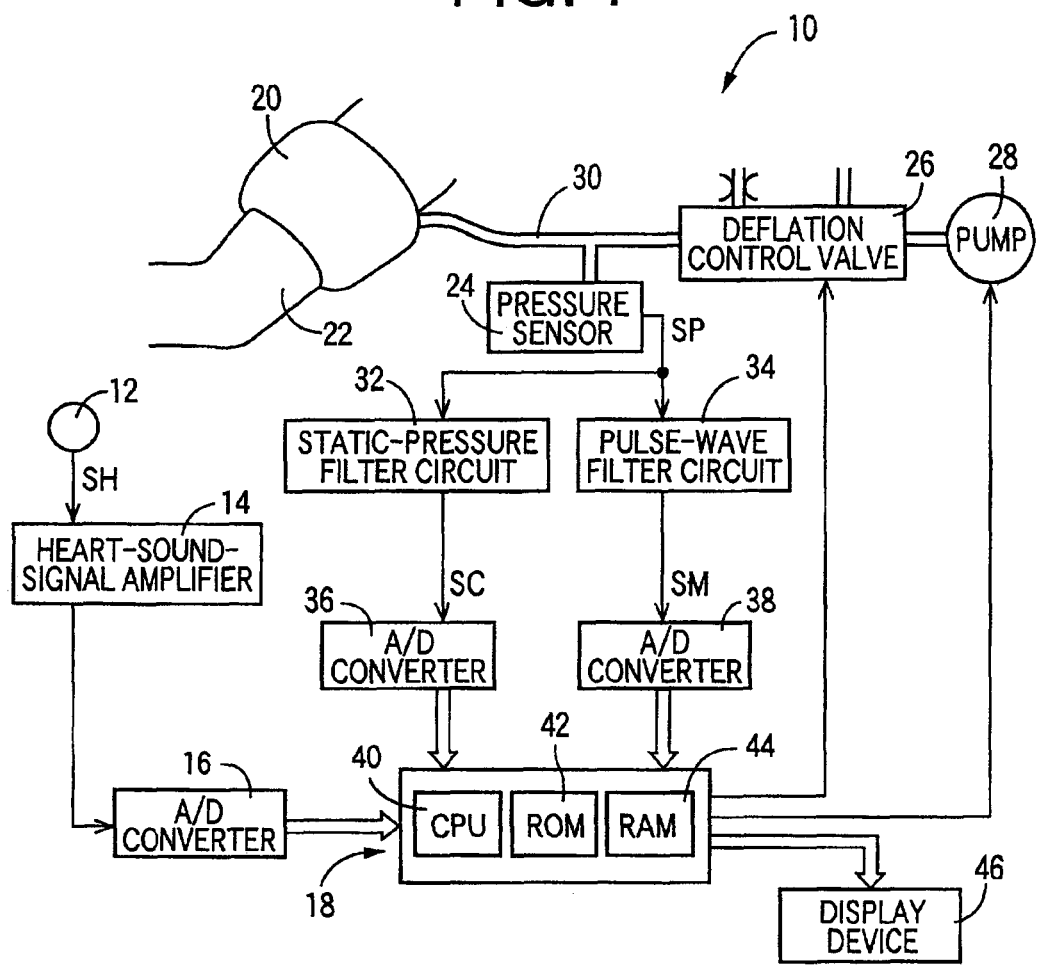
FIG. 1 is a view showing a construction of a pulse-wave-propagation-velocity-related-information obtaining apparatus functioning as a pulse-wave-characteristic-point determining apparatus, to which the present invention is applied.

Hereinafter, there will be described in detail a preferred embodiment of the present invention, by reference to the drawings. FIG. 1 is a view showing a construction of a pulse-wave-propagation-velocity-related-information obtaining apparatus 10 functioning as a pulse-wave-characteristic-point determining apparatus, to which the present invention is applied.

The present apparatus includes a heart-sound microphone 12 functioning as a second heartbeat-synchronous-signal detecting device. The microphone 12 is attached, with an adhesive tape, not shown, to a chest of a living subject, not shown. The microphone 12 is for detecting heart sounds as a heartbeat-synchronous signal. The microphone 12 incorporates a piezoelectric element, not shown, which converts the heart sounds produced from the heart of the subject, into an electric signal, i.e., a heart-sound signal SH. A heart-sound-signal amplifier 14 includes four different filters, not shown, that attenuate, for clearly recording a high-pitched sound component of the heart sounds, a low-pitched sound component thereof having a high energy. The heart-sound signal SH amplified and filtered by the heart-sound-signal amplifier 14 is sent to an electronic control device 18 via an A/D (analog-to-digital) converter 16.

The present apparatus additionally includes a cuff 20 which includes a belt-like cloth bag and a rubber bag accommodated in the cloth bag and which is wound around, e.g., an upper portion 22 of a right arm of the subject. The cuff 20 is connected to a pressure sensor 24, a deflation control valve 26, and an air pump 28 via a piping 30. The deflation control valve 26 is selectively placed in a pressure-supply position in which the control valve 26 permits a pressurized air to be supplied from the air pump 28 to the cuff 20, a slow-deflation position in which the control valve 26 permits the pressurized air to be slowly discharged from the cuff 20, and a quick-deflation position in which the control valve 26 permits the pressurized air to be quickly discharged from the cuff 20.

The pressure sensor 24 detects an air pressure $P_K$ in the cuff 10, and supplies a pressure signal SP representing the detected pressure $P_K$, to each of a static-pressure filter circuit 32 and a pulse-wave filter circuit 34. The static-pressure filter circuit 32 includes a low-pass filter and extracts, from the pressure signal SP, a static-pressure component contained in the pressure signal SP, i.e., a cuff-pressure signal SC representing the static or pressing pressure in the cuff 20. The cuff-pressure signal SC is supplied to the control device 18 via an A/D converter 36. The pulse-wave filter circuit 34 includes a band-pass filter and extracts, from the pressure signal SP, an oscillating component, i.e., a cuff-pulse-wave signal SM. The cuff-pulse-wave signal SM is supplied to the control device 18 via an AID converter 38. The cuff-pulse-wave signal SM represents a brachial-artery pulse wave, BW, as a heartbeat-synchronous signal produced from the upper arm 22 in synchronism with heartbeat of the subject. The pulse-wave filter circuit 34 functions as a first pulse-wave detecting device or a first heartbeat-synchronous-signal detecting device.

The control device 18 is provided by a so-called microcomputer including a CPU (central processing unit) 40, a ROM (read only memory) 42, a RAM (random access memory) 44, and an I/O (input and output) port, not shown. The CPU 40 processes signals according to the control programs pre-stored in the ROM 42 by utilizing the temporary-storage function of the RAM 44, and generates respective drive signals via the I/O port to respective drive circuits, not shown, so as to control the deflation control valve 26 and the air pump 28. More specifically described, the CPU 40 controls the deflation control valve 26 and the air pump 28 so as to change and maintain the pressure in the cuff 20 to and at a pre-set pulse-wave-detect pressure, e.g., 60 mmHg which is sufficiently lower than a diastolic blood pressure of the subject and which assures that the cuff-pulse-wave signal SM extracted by the pulse-wave filter circuit 34 has a sufficiently high strength or voltage. In addition, the CPU 40 obtains pulse-wave-propagation-velocity-related information based on the signals supplied to the electronic device 18, and operates a display device 46 to display the thus obtained information.

Figure 2:
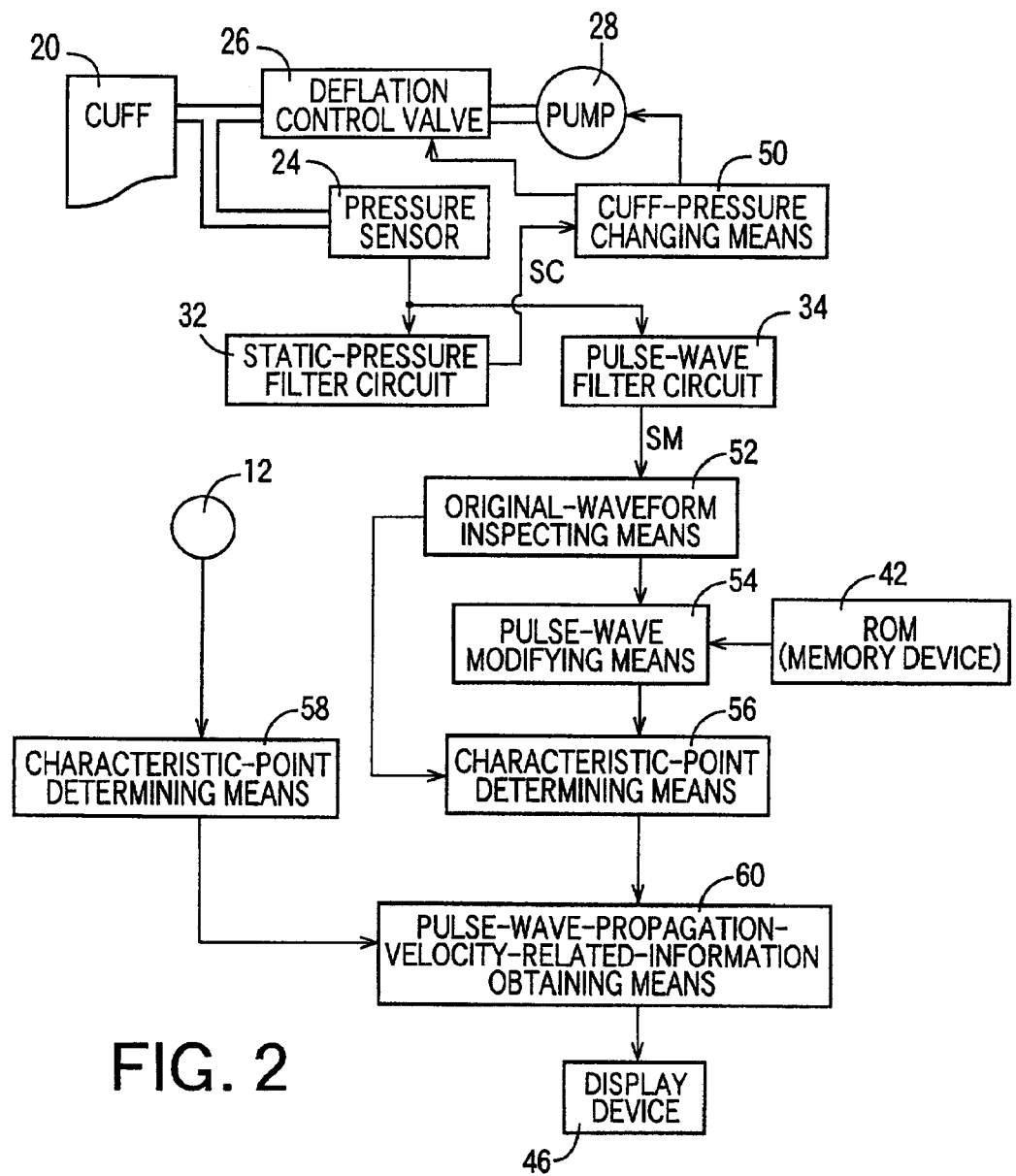
FIG. 2 is a block diagram for explaining essential control functions of an electronic control device of the apparatus of FIG. 1.

FIG. 2 is a block diagram showing essential control functions of the electronic control device 18. A cuff-pressure changing means 50 recognizes the pressing pressure in the cuff 20, based on the cuff-pressure signal SC supplied from the static-pressure filter circuit 32, and controls the deflation control valve 26 and the air pump 28 so as to change and maintain the pressing pressure of the cuff 20 to and at the pre-set pulse-wave-detect pressure.

An original-waveform inspecting means 52 inspects an original wave BW of the brachial-artery pulse wave represented by the cuff-pulse-wave signal SM continuously supplied from the pulse-wave filter circuit 34 in the state in which the pressing pressure of the cuff 20 is maintained at the pulse-wave-detect pressure by the cuff-pressure changing means 50, and judges whether a prescribed characteristic point of the original waveform BW of the pulse wave is clearly recognizable. The characteristic point may be a rising point, a maximal point, or a notch of the pulse wave, or any other point that may be determined when physical information is obtained from the pulse wave. This judgment is made as follows: First, the brachial-artery pulse wave BW, i.e., signal SM is subjected to frequency analysis so as to determine an intensity of a signal component having frequencies of the characteristic point, the frequencies being pre-stored in the ROM 42, and then the characteristic point is judged as being clear if the determined intensity of the signal component is greater than a reference value.

A pulse-wave modifying means 54 modifies, if the original-waveform inspecting means 52 has judged that the characteristic point of the original waveform BW of the brachial-artery pulse wave supplied from the pulse-wave filter circuit 34, is not clear, the original waveform BW of the pulse wave, according to a pre-determined relationship, pre-stored in the ROM 42 functioning as a memory device. Thus, the original waveform BW of the brachial-artery pulse wave is modified into a modified waveform BW' of the pulse wave. The pre-stored relationship is pre-determined based on at least one brachial-artery pulse wave BW whose characteristic point has been judged as being not clear, and at least one reference pulse wave (e.g., at least one carotid-artery pulse wave, CW) whose characteristic point has been judged as being clear, and it is used to modify a waveform BW of a brachial-artery pulse wave whose characteristic point is not clear, into a waveform of a reference pulse wave whose characteristic point is clear. This relationship may be expressed using a transfer function, G, between brachial-artery pulse wave BW as input, and reference pulse wave as output. This transfer function may be obtained using an autoregressive model (e.g., an autoregressive exogenous (ARX) model), as will be described below. In the following description, it is assumed that the reference pulse wave is a carotid-artery pulse wave CW and the characteristic point is a notch of the carotid-artery pulse wave CW.

The relationship between brachial-artery pulse wave BW as input and carotid-artery pulse wave CW as output can be expressed by various autoregressive models, for example, by the following Expression 1:

$$BW(s)+a_1 BW(s-1)+ \ldots +a_{na}BW(s-na)=CW(s)+b_1 CW(s-1)+b_2 CW(s-2)+ \ldots +b_{nb}CW(s-nb) \quad \text{(Expression 1)}$$

In Expression 1, the parenthesized symbol indicates a sampling order; symbol 's' indicates a time of detection of a prescribed reference point of brachial-artery pulse wave BW or the carotid-artery pulse wave CW; and symbols 'BW(s)', 'CW(s)' indicate respective sampled data (respective signal magnitudes) of the brachial-artery pulse wave BW or the carotid-artery pulse wave CW that are iteratively obtained at a sampling period. In addition, symbols 'na', 'nb' indicate respective sampling numbers that are experimentally determined beforehand; for example, (na, nb)=(4, 6) or (10, 10).

Expression 1 can be transformed using a time-shift operator, q, into the following Expression 2:

$$(1+a_1 q^{-1}+ \ldots +a_{na}q^{-na})BW(s)=(1+b_1 q^{-1}+ \ldots +b_{nb}q^{-nb})CW(s) \quad \text{(Expression 2)}$$

Expression 2 can be transformed into the following Expression 3:

$$CW(s)=\{(1+a_1 q^{-1}+ \ldots +a_{na}q^{-na})/(1+b_1 q^{-1}+ \ldots +b_{nb}q^{-nb})\}BW(s) \quad \text{(Expression 3)}$$

The transfer function G(s) can be expressed by the following Expression (4):

$$G(s)=(1+a_1 q^{-1}+ \ldots +a_{na}q^{-na})/(1+b_1 q^{-1}+ \ldots +b_{nb}q^{-nb}) \quad \text{(Expression 4)}$$

The relationship represented by Expression 3 is pre-stored in the ROM 42, and a modified waveform BW' of the brachial-artery pulse wave is determined by replacing the right-hand side of Expression 3 with the magnitude of the cuff-pulse-wave signal SM that is continuously supplied from the pulse-wave filter circuit 34 and represents the pulse wave BW. The modified waveform BW' of the brachial-artery pulse wave corresponds to the waveform of the carotid-artery pulse wave CW.

In the case where the transfer function G(s) is expressed by Expression 4, coefficients, $a_1, \ldots, a_{na}, b_1, \ldots, b_{nb}$, of Expression 4 are determined as follows: First, all terms of the right-hand and left-hand sides of Expression 1 are replaced with corresponding magnitudes (sampled data) of brachial-artery pulse wave BW and carotid-artery pulse wave CW, so as to obtain an equation, and then this operation is repeated the same number of times as the total number (=na+nb) of the above coefficients, or more times, so as to obtain the same number of equations, or more equations. Finally, the coefficients $a_1, \ldots, a_{na}, b_1, \ldots, b_{nb}$ are determined, by the technique of least square, from those equations.

Figure 3:
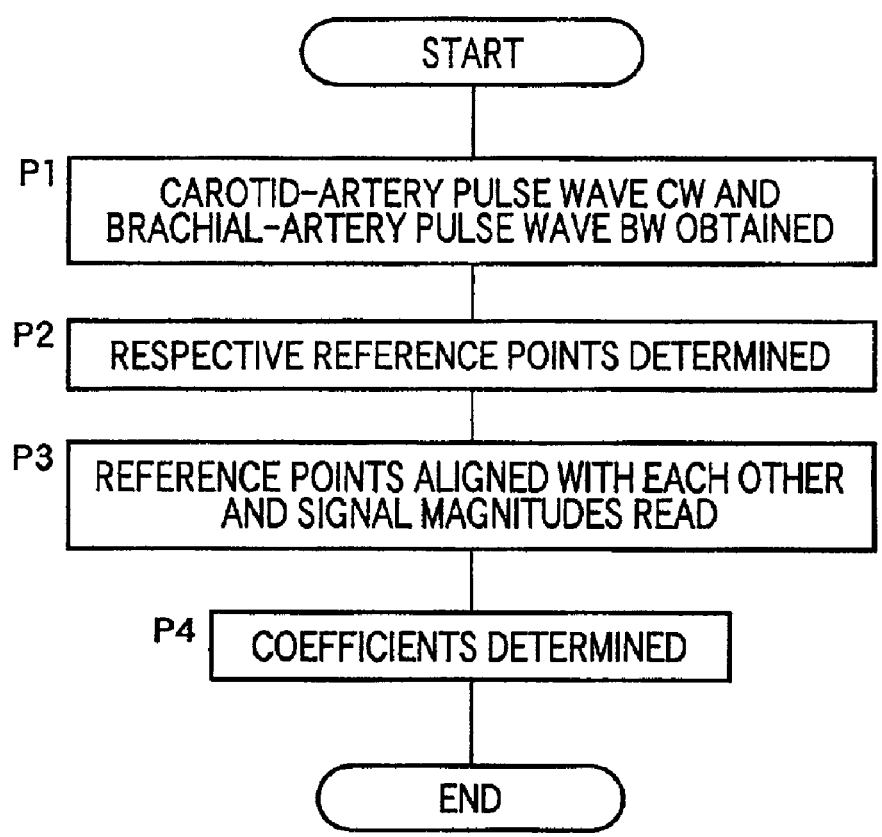
FIG. 3 is a flow chart representing a method of determining coefficients of a transfer function, G(s)

FIG. 3 is a flow chart representing a method of determining the coefficients $a_1, \ldots, a_{na}, b_1, \ldots, b_{nb}$ of the transfer function G(s). First, at Step P1, a carotid-artery pulse wave CW and a brachial-artery pulse wave BW are obtained from a patient whose brachial-artery pulse wave BW has been judged as not showing a clear notch. Those pulse waves may be obtained using such a device which is identical with the pulse-wave-propagation-velocity-related-information obtaining apparatus shown in FIG. 1, except that the heart-sound microphone 12 is replaced with a carotid-pulse-wave sensor.

Subsequently, respective reference points are determined on the thus obtained carotid-artery pulse wave CW and brachial-artery pulse wave BW (at Step P2). A point which can be determined more accurately than the notch as the characteristic point, is selected as each reference point. For example, a rising point or a maximal point of each pulse wave is selected as each reference point.

Figure 4:
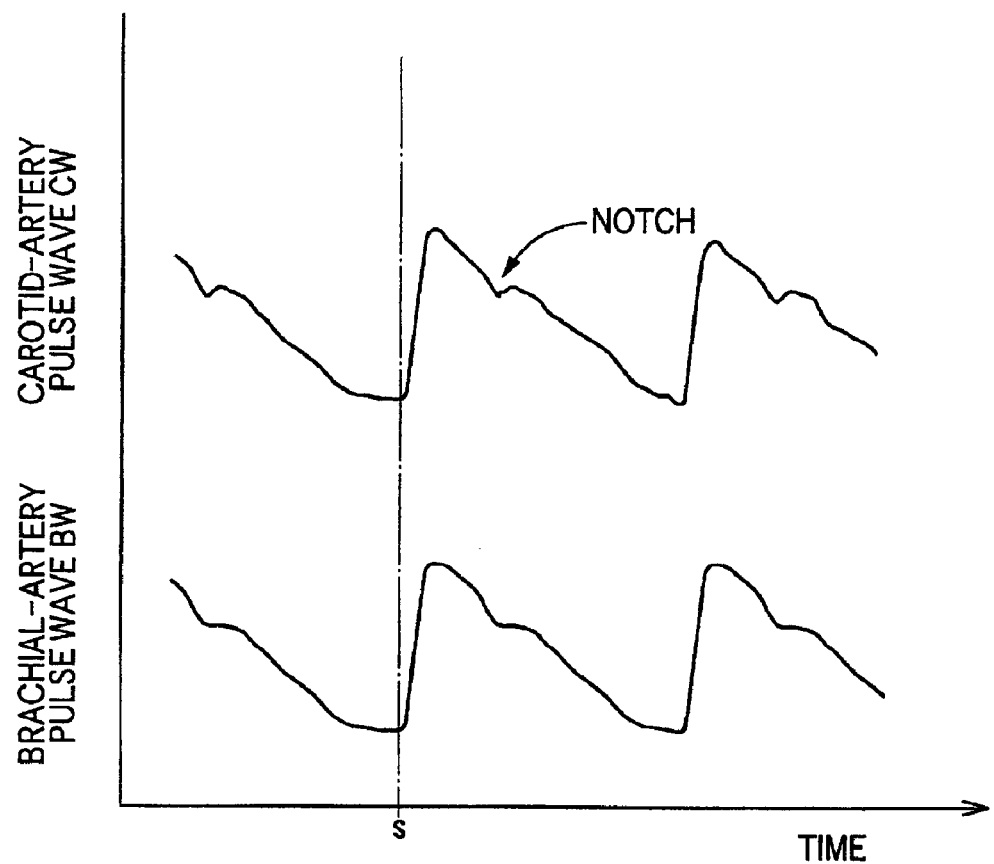
FIG. 4 is a graph showing a carotid-artery pulse wave, CW, and a brachial-artery pulse wave, BW, read in at Step P1, in a state in which respective rising points of the two pulse waves are aligned with each other at Step P3.

Next, the respective reference points of the carotid-artery pulse wave CW and the brachial-artery pulse wave BW are aligned with each other so as to periodically read or samples respective magnitudes or data of the two pulse waves (or the corresponding electric signals) at a sampling period (at Step P3). FIG. 4 shows that at Step P3, respective rising points of the carotid-artery pulse wave CW and the brachial-artery pulse wave BW, as the reference points, are aligned with each other.

Next, all terms of the right-hand and left-hand sides of Expression 1 are replaced with corresponding magnitudes of the brachial-artery pulse wave BW and the carotid-artery pulse wave CW that have been read, or will be read, at the sampling period, or a period equal to the product of the sampling period and a pre-selected integer, before or after the aligned reference points, s, so as to obtain an equation. This operation is repeated the same number of times as the total number of the above coefficients na, nb, or more times, so as to obtain the same number of equations, or more equations. Finally, the coefficients $a_1, \ldots, a_{na}, b_1, \ldots, b_{nb}$ are determined, by the technique of least square, from those equations.

The method represented by the flow chart of FIG. 3 is carried out on a number of patients so as to determine a corresponding number of groups of coefficients $a_1, a_{na}, b_1, \ldots, b_{nb}$, and finally determine a single group of average coefficients $a_{1ave}, \ldots, a_{naave}, b_{1ave}, \ldots, b_{nbave}$. The ROM 42 stores the relationship represented by Expression 3 expressed using the thus obtained average coefficients $a_{1ave}, \ldots, a_{naave}, b_{1ave}, \ldots, b_{nbave}$. Since the relationship or Expression 3 is determined based on the respective magnitudes of the two pulse waves that are specified at Step P3 after the two reference points are aligned with each other at Step P2, respective data points of the modified brachial-artery waveform BW' determined using Expression 3 are not time-wise moved relative to the corresponding data points of the original brachial-artery waveform BW, and only the respective magnitudes of the original data points are modified to make clear the notch.

Back to FIG. 2, a first pulse-wave-characteristic-point determining means 56 determines, if the original-waveform inspecting means 52 judges that the original waveform BW of the brachial-artery pulse wave supplied from the pulse-wave filter circuit 34 has a clear characteristic point, a time of occurrence of the characteristic point of the original waveform; and, if not, the first determining means 56 determines a time of occurrence of the characteristic point, i.e., notch of the modified waveform BW' of the brachial-artery pulse wave determined by the pulse-wave modifying means 54.

A second pulse-wave-characteristic-point determining means 58 determines, on a waveform of the heart-sound signal SH supplied from the heart-sound microphone 12, a time of occurrence of a starting point of a second heart sound II corresponding to the notch of the brachial-artery pulse wave BW.

A pulse-wave-propagation-velocity-related-information obtaining means 60 calculates a time difference between the time of occurrence of the starting point of second heart sound II determined by the second pulse-wave-characteristic-point determining means 58, and the time of occurrence of the notch of the original waveform BW or modified waveform BW' of the brachial-artery pulse wave determined by the first pulse-wave-characteristic-point determining means 56, and determines the thus calculated time difference as a pulse-wave propagation time DT. Alternatively, the obtaining means 60 additionally calculates a pulse-wave propagation velocity PWV, based on the thus calculated pulse-wave propagation time DT, according to the following Expression 5, in which L is a distance from the subject's heart to the position where the cuff 20 is worn on the subject, and is replaced with a constant value that is experimentally obtained beforehand:

$$PWV = L/DT \qquad \text{(Expression 5)}$$

The display device 46 displays the thus calculated pulse-wave propagation time DT and/or the thus calculated pulse-wave propagation velocity PWV.

Figure 5:
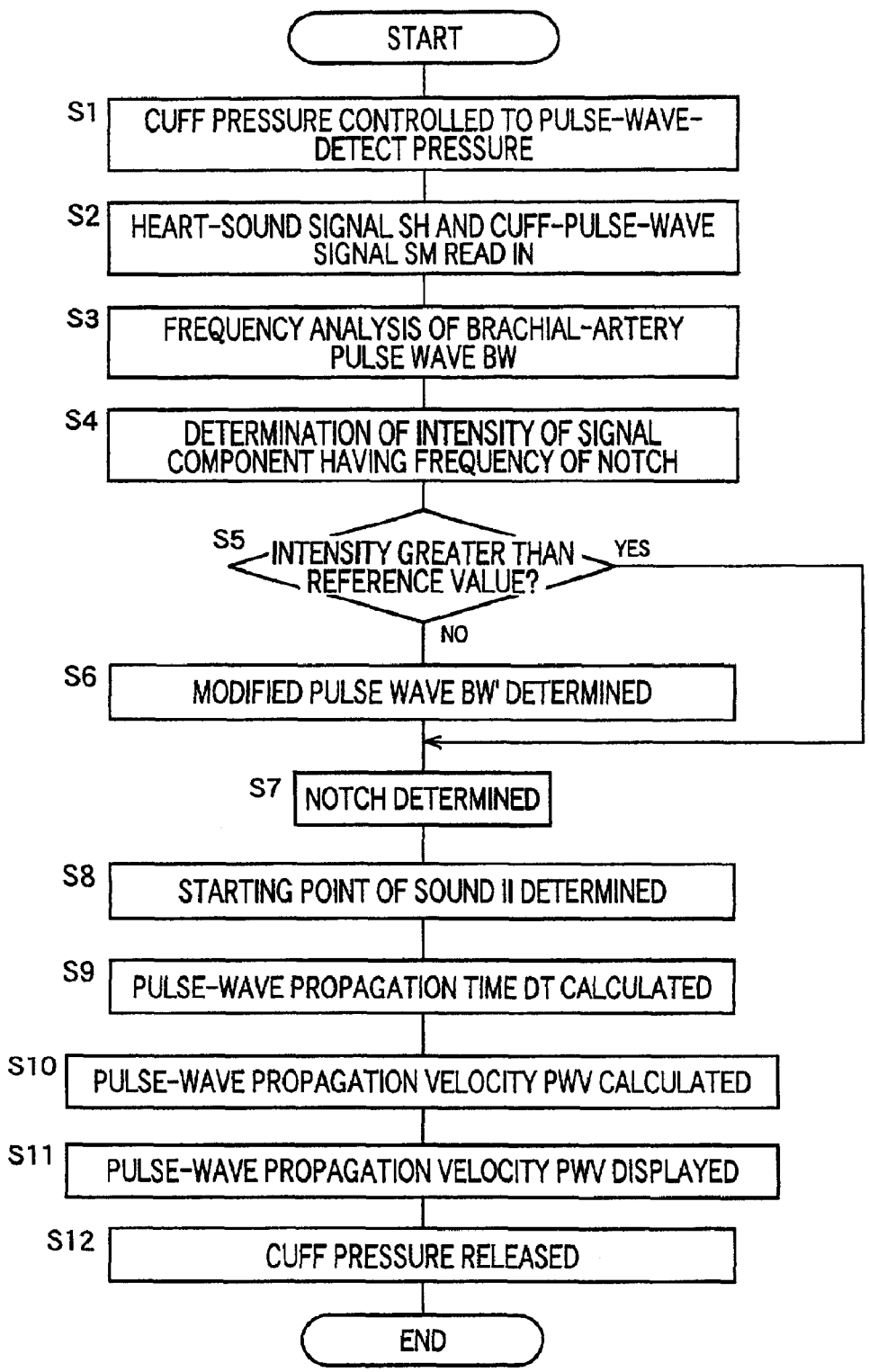
FIG. 5 is a flow chart representing the control functions of the electronic control device, shown in FIG. 2.

FIG. 5 is a flow chart representing the control functions of the control device 18, shown in FIG. 2.

In FIG. 5, at Step S1 (hereinafter, "Step" is omitted, if appropriate) corresponding to the cuff-pressure changing means 50, the control device 18 controls the deflation control valve 26 and the air pump 28 to change and maintain the pressing pressure of the cuff 20 to and at the pulse-wave-detect pressure. Subsequently, at S2, the control device 18 periodically reads in respective magnitudes of the heart-sound signal SH and the cuff-pulse-wave signal SM, at the predetermined sampling period, for a predetermined time duration corresponding to one beat of the subject's heart.

Next, the control goes to S3 to S5 corresponding to the original-waveform inspecting means 52. First, at S3, the control device subjects the brachial-artery pulse wave BW, i.e., the cuff-pulse-wave signal SM read in at S2, to frequency analysis, so as to obtain a spectrum. Subsequently, at S4, the control device determines, from the thus obtained spectrum, an intensity of a signal component having prescribed frequencies of notch that are considerably high in all frequencies of the pulse wave BW, i.e., the pulse-wave signal SM. If the pulse wave BW has a clear notch, the intensity of the signal component having the prescribed frequencies should be great; and if not, the intensity should be small. Therefore, at S5, the control device judges whether the intensity of the signal component determined at S4 is greater than a reference value, and thereby judges whether the pulse wave BW has a clear notch.

Figure 6:
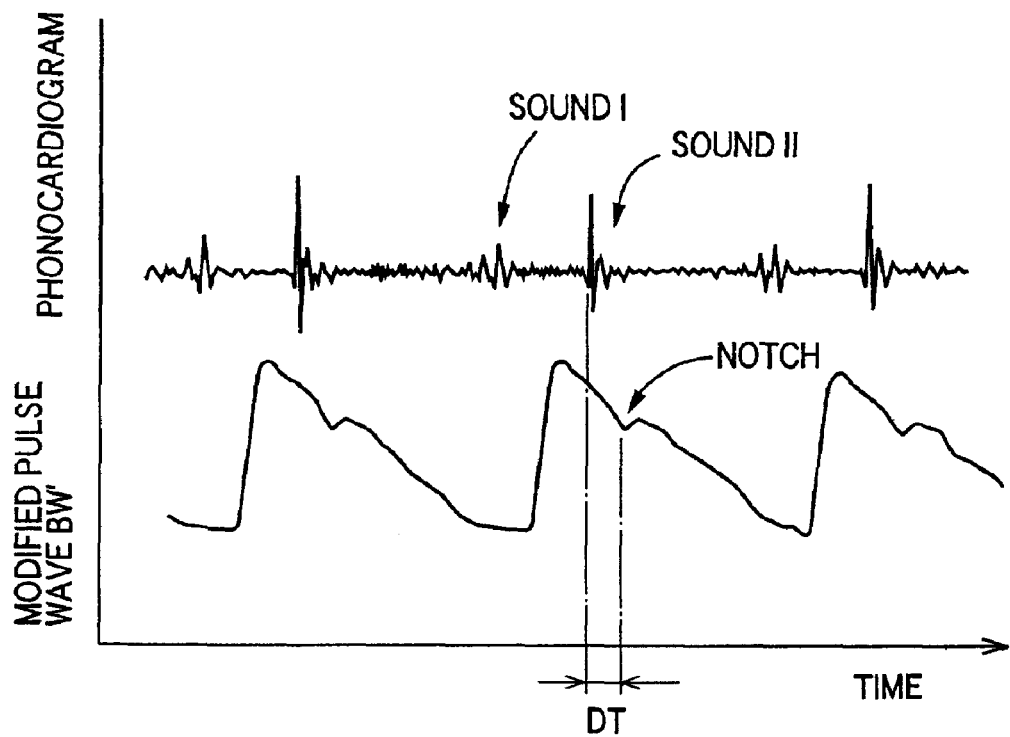
FIG. 6 is a graph showing an example of a phonocardiogram read in at Step S2 of FIG. 5 and an example of a modified pulse wave, BW', determined at Step S6.

A positive judgment made at S5 means that a time of occurrence of the notch of the brachial-artery pulse wave BW can be accurately determined without modifying the pulse wave BW. Hence, the control goes directly to S7 and the following steps. On the other hand, if a negative judgment is made at S5, the control goes to S6 corresponding to the pulse-wave modifying means 54. At S6, the control device modifies the brachial-artery pulse wave BW to a modified pulse wave BW'0 whose waveform corresponds to that of the carotid-artery pulse wave CW, by replacing the terms of Expression 3 as the relationship pre-stored in the ROM 42, with the respective magnitudes of the cuff-pulse-wave signal SM periodically read in at S2. FIG. 6 shows respective examples of the heart sounds read in at S2 and the modified pulse wave BW' determined at S6.

Then, the control goes to S7 corresponding to the first pulse-wave-characteristic-point determining means 56. At S7, the control device determines a notch of the brachial-artery pulse wave BW or the modified pulse wave BW'. More specifically described, in the case where a positive judgment is made at S5, the control device determines a notch of the pulse wave BW as it is, i.e., the cuff-pulse-wave signal SM read in at S2; and in the case where a negative judgment is made at S5, the control device determines a notch of the modified pulse wave BW' determined at S6. The notch may be determined, for example, as follows: First, a maximal point of the pulse wave BW or the modified pulse wave BW' is determined, and a minimal point of the waveform following the maximal point is determined as the notch.

Then, the control goes to S8 corresponding to the second pulse-wave-characteristic-point determining means 58. At S8, the control device determines a starting point of a second heart sound II represented by the heart-sound signal SH read in at S2. The starting point of the second heart sound II may be determined, for example, as follows: First, the amplitude or magnitude of the heart-sound signal SH, as measured from a base line (i.e., a magnitude of the signal free of the heart sounds), is squared, and a point on the squared waveform where the amplitude or magnitude thereof first exceeds a predetermined threshold, TH, is determined as the starting point of the second heart sound II.

Subsequently, the control goes to S9 to S11 corresponding to the pulse-wave-propagation-velocity-related-information obtaining means 60. At S9, the control device calculates, as a pulse-wave propagation time DT, a time difference between a time of occurrence of the starting point of the second heart sound II determined at S8 and a time of occurrence of the notch determined at S7, as illustrated in FIG. 6. Then, at S10, the control device calculates a pulse-wave propagation velocity PW, by replacing the parameter DT of Expression 5 with the pulse-wave propagation time DT calculated at S9. At S11, the control device controls the display device 46 to display the pulse-wave propagation velocity PWV calculated at S10.

After the pulse-wave propagation velocity PWV is displayed, the control goes to S12 where the control device switches the deflection control valve 26 to its quick-deflation position, and stops the air pump 28, so as to release the pressure from the cuff 12. Thus, the present routine is finished.

In the present embodiment employing the flow chart shown in FIG. 5, the control device 18 determines, at S6 (the pulse-wave modifying means 54), the modified pulse wave BW' by modifying the brachial-artery pulse wave BW actually detected by the pulse-wave filter circuit 34, according to the predetermined relationship between brachial-artery pulse wave BW, and carotid-pulse pulse wave CW whose notch is clear, the relationship being represented by Expression 3. Therefore, even if the brachial-artery pulse wave BW actually detected may not have a clear notch, the modified pulse wave BW' has a clear notch. Therefore, if the control device judges, at S3 to S5 (the original-waveform inspecting means 52), that the brachial-artery pulse wave BW as it is does not have a clear notch, then the control device determines, at S7 (the first pulse-wave-characteristic-point determining means 56), the clear notch of the modified pulse wave BW'. Thus, in each case, the control device can accurately determine a notch.

In addition, in the embodiment employing the flow chart shown in FIG. 5, the control device can accurately determine the notch at S7 (the first pulse-wave-characteristic-point determining means 56), and accordingly the control device can accurately obtain, at S9 and S10 (the pulse-wave-propagation-velocity-related-information obtaining means 60), the pulse-wave-propagation-velocity-related information, e.g., the pulse-wave propagation time as the time difference between the time of occurrence of the notch and the time of occurrence of the starting point of the second heart sound II detected by the heart-sound microphone 12.

While the present invention has been described in its embodiment by reference to the drawings, the invention may otherwise be embodied.

For example, in the illustrated embodiment, the coefficients in Expression 3 are a group of average coefficients obtained from a great number of groups of coefficients that are respectively determined for a great number of individual persons. However, it is possible to employ, as the coefficients of Expression 3, a group of coefficients determined for each individual person as they are.

In addition, in the illustrated embodiment, the brachial-artery pulse wave BW is detected as the first pulse wave. However, it is possible to detect a radial-artery pulse wave or a finger-tip pulse wave as the first pulse wave. In the case where the radial-artery pulse wave is detected as the first pulse wave, it is possible to employ, as a device for detecting the pulse wave, a pressure-pulse-wave sensor which is adapted to be worn on a position right above a radial artery of a wrist. And, in the case where the finger-tip pulse wave is detected as the first pulse wave, it is possible to employ, as a device for detecting the pulse wave, a pulse-wave sensor which is adapted to be worn on a tip portion of a finger so as to detect pulsation.

Moreover, the flow chart shown in FIG. 5 may be modified to additionally include, between S4 and S5, another step where, if the intensity of the signal component, determined at S4, is lower than a predetermined value indicating that there is substantially no information about notch, the control device aborts the routine of FIG. 5 without obtaining pulse-wave-propagation-velocity-related information. In this case, the control device can avoid an operation for obtaining inaccurate pulse-wave-propagation-velocity-related information.

While the present invention has been described in detail in its embodiment by reference to the drawings, it is to be understood that the present invention is not limited to the details of the embodiment but may be embodied with various changes and improvements that may occur to a person skilled in the art.

What is claimed is:

1. An apparatus for determining a characteristic point of a pulse wave detected from a living subject, the apparatus comprising:
    a pulse-wave detecting device which detects a first pulse wave from a prescribed portion of the subject;
    a pulse-wave modifying means for modifying a waveform of the first pulse wave detected by the pulse-wave detecting device according to a predetermined relationship between first pulse wave and a second pulse wave, whose characteristic point is clear; and
    a characteristic-point determining means for determining a characteristic point of the modified waveform of the first pulse wave.

2. An apparatus for obtaining pulse-wave-propagation-velocity-related information that is related to a velocity at which a pulse wave propagates in a living subject, the apparatus comprising:
    a pulse-wave detecting device which detects, as a first heartbeat-synchronous signal, a first pulse wave from a first prescribed portion of the subject;
    a pulse-wave modifying means for modifying a waveform of the first pulse wave detected by the pulse-wave detecting device according to a predetermined relationship between first pulse wave and a second pulse wave, whose characteristic point is clear;
    a characteristic-point determining means for determining a characteristic point of the modified waveform of the first pulse wave;
    a heartbeat-synchronous-signal detecting device which detects, from a second prescribed portion of the subject that is different from the first prescribed portion, a second heartbeat-synchronous signal; and
    a pulse-wave-propagation-velocity-related-information obtaining means for obtaining the pulse-wave-propagation-velocity-related information, based on a time of occurrence of the determined characteristic point of the modified waveform of the first pulse wave and a time of occurrence of a prescribed point of the second heartbeat-synchronous signal detected by the heartbeat-synchronous-signal detecting device.

3. An apparatus according to claim 2, further comprising a display device which displays the pulse-wave-propagation-velocity-related information obtained by the pulse-wave-propagation-velocity-related-information obtaining means.

4. An apparatus according to claim 2, wherein the heartbeat-synchronous-signal detecting device comprises a heart-sound microphone which detects a heart sound produced from the heart of the subject.

5. An apparatus according to claim 4, wherein the pulse-wave detecting device comprises an inflatable cuff which detects a brachial-artery pulse wave produced from an upper arm of the subject.

6. An apparatus according to claim 5, wherein the pulse-wave-propagation-velocity-related-information obtaining means determines, as the pulse-wave-propagation-velocity-related information, a pulse-wave propagation time equal to a time difference between the time of occurrence of the prescribed point of the heart sound as the second heartbeat-synchronous signal detected by the heart-sound microphone as the heartbeat-synchronous-signal detecting device and the time of occurrence of the determined characteristic point of the modified waveform of the brachial-artery pulse wave as the first pulse wave.

7. An apparatus according to claim 2, further comprising a memory device which stores the predetermined relationship.

8. An apparatus according to claim 2, further comprising a point determining means for determining the prescribed point of the second heartbeat-synchronous signal detected by the heartbeat-synchronous-signal detecting device.

9. An apparatus according to claim 2, further comprising a waveform inspecting means for inspecting the waveform of the first pulse wave detected by the pulse-wave detecting device, and judging whether the waveform of the first pulse wave has a clear characteristic point, wherein the pulse-wave modifying means modifies, when the waveform inspecting means judges that the waveform of the first pulse wave does not have the clear characteristic point, the waveform of the first pulse wave according to the predetermined relationship between first pulse wave, and second pulse wave whose characteristic point is clear.

* * * * *